United States Patent
Kameishi et al.

(10) Patent No.: US 9,629,611 B2
(45) Date of Patent: Apr. 25, 2017

(54) ULTRASOUND DIAGNOSIS APPARATUS FOR SUBSTANTIALLY REDUCING TAP CONCENTRATION

(75) Inventors: Wataru Kameishi, Nasushiobara (JP); Hiroyuki Shibanuma, Yaita (JP); Satoshi Kamiyama, Otawara (JP); Shuta Fujiwara, Nasushiobara (JP); Gen Nagano, Nasuhiobara (JP); Takayuki Shiina, Otawara (JP)

(73) Assignees: TOSHIBA MEDICAL SYSTEMS CORPORATION, Otawara-Shi, Tochigi-Ken (JP); KABUSHIKI KAISHA TOSHIBA, Tokyo (JP)

(*) Notice: Subject to any disclaimer, the term of this patent is extended or adjusted under 35 U.S.C. 154(b) by 200 days.

(21) Appl. No.: 13/993,029

(22) PCT Filed: Feb. 3, 2012

(86) PCT No.: PCT/JP2012/052463
§ 371 (c)(1),
(2), (4) Date: Jun. 10, 2013

(87) PCT Pub. No.: WO2012/108344
PCT Pub. Date: Aug. 16, 2012

(65) Prior Publication Data
US 2013/0338499 A1    Dec. 19, 2013

(30) Foreign Application Priority Data
Feb. 7, 2011   (JP) .................................. 2011-023512

(51) Int. Cl.
*A61B 8/14* (2006.01)
*A61B 8/08* (2006.01)
(Continued)

(52) U.S. Cl.
CPC ............ *A61B 8/488* (2013.01); *G01S 7/5203* (2013.01); *G01S 7/52047* (2013.01);
(Continued)

(58) Field of Classification Search
None
See application file for complete search history.

(56) References Cited

U.S. PATENT DOCUMENTS 4,628,738 A * 12/1986 Burckhardt et al. ............ 73/626
5,398,216 A *  3/1995 Hall et al. ...................... 367/90
(Continued)

FOREIGN PATENT DOCUMENTS

JP    5-200028 A    8/1993
JP    7-124161 A    5/1995
(Continued)

OTHER PUBLICATIONS

International Search Report Mailed on Feb. 28, 2012 for Corresponding International Application No. PCT/JP2012/052463.

*Primary Examiner* — James Kish
(74) *Attorney, Agent, or Firm* — Kenichiro Yoshida

(57) ABSTRACT

Saturation of received signals and generation of artifacts that are associated with tap concentration are prevented from occurring even if the differences in the delay amount between each of transducers are small. The ultrasound diagnosis apparatus comprises a plurality of ultrasound transducers, a plurality of taps, a delay amount calculator, a channel distributor, and a delay processor. The delay amount calculator calculates a first delay amount. The channel distributor specifies the minimum delay amount and the maximum delay amount from the first delay amount. Further, the channel distributor divides the range from the minimum delay amount to the maximum delay amount by the number of taps, and relates each to a tap. The channel
(Continued)

distributor also inputs a signal output from an ultrasound transducer to the tap related to the divided range including the corresponding first delay amount. The delay processor relates the tap to a previously set second delay amount, and conducts delay processing on the signal input in each of the taps based on the related second delay amount.

6 Claims, 14 Drawing Sheets

(51) Int. Cl.
*G10K 11/34* (2006.01)
*G01S 15/89* (2006.01)
*G01S 7/52* (2006.01)

(52) U.S. Cl.
CPC ...... *G01S 15/8913* (2013.01); *G01S 15/8915* (2013.01); *G01S 15/8979* (2013.01); *G10K 11/346* (2013.01)

(56) References Cited

U.S. PATENT DOCUMENTS

2005/0237858 A1* 10/2005 Thomenius et al. .......... 367/155
2010/0030081 A1   2/2010 Masuzawa et al.

FOREIGN PATENT DOCUMENTS

| | | |
|---|---|---|
| JP | 2005-66055 A | 3/2005 |
| JP | 2005-328885 A | 12/2005 |
| JP | 2010-81965 A | 4/2010 |
| WO | 2008/108115 A1 | 9/2008 |

* cited by examiner

ULTRASOUND DIAGNOSIS APPARATUS FOR SUBSTANTIALLY REDUCING TAP CONCENTRATION

TECHNICAL FIELD

The embodiments of the present invention relate to an ultrasound diagnosis apparatus.

BACKGROUND ART

The operational modes of an ultrasound diagnosis apparatus include one that uses continuous waves like a continuous wave Doppler (hereinafter referred to as "SCW") mode used for measurement of a blood flow velocity, and the like. In such a mode using continuous waves, delay focus is performed by transmitting continuous waves to a subject, and providing the delay amount within one carrier frequency cycle to a plurality of received signals obtained from the reflected waves thereof.

Conventionally, by preparing approximately 8 to 16 taps with a fixed amount of delay within one carrier frequency cycle and selectively providing the received signals with appropriate delay amount from the taps, the delay has been added to the signals.

However, in this case, all the taps are not always selected. In particular, the deeper the focus point related to the reception of ultrasound waves (hereinafter simply referred to as "focus point") is, the smaller the delay amount to provide between ultrasound transducers. It is specifically described below with regards to the case.

For example, FIG. 11 and FIG. 12 show the positional relationship between the focus point and each transducer for focus points at different depths, with a delay amount corresponding to each transducer. FIG. 11A shows the positional relationship between a focus point FA, where the depth is shallow, and each transducer CH0-CHn. Further, FIG. 11B is a graph of the delay amount corresponding to each transducer CH0-CHn in this case, with the horizontal axis as each transducer CH and the vertical axis as a delay amount td. Similarly, FIG. 12A shows the positional relationship between a focus point FB, where the depth is deep, and each transducer CH0-CHn. Furthermore, FIG. 12B is a graph of the delay amount corresponding to each transducer CH0-CHn in this case, with the horizontal axis as each transducer CH and the vertical axis as the delay amount td.

For example, describing FIG. 11A as an example, the delay amount corresponding to each transducer is calculated based on the distance between the focus point FA and each transducer on the basis of the transducer CHn at the position farthest from the focus point FA (amount of delay 0). In this case, a distance LAj between the focus point FA and the transducer CHj is the shortest. Therefore, as shown in FIG. 11B, the delay amount corresponding to the transducer CHj is the largest. Hereinafter, the delay amount in this case is defined as a maximum delay amount tdMaxA.

It is also similar in the case when the depth is deep as in FIG. 12A. That is, the delay amount corresponding to each transducer is calculated based on the distance between the focus point FB and each transducer, as the basis of the transducer CHn at the position farthest from the focus point FB. However, as the depth of the focus point deepens, the difference between a distance LBn to the transducer CHn farthest from the focus point FB and a distance LBj to the transducer CHj closest to the focus point FB becomes smaller. Therefore, as shown in FIG. 12B, a maximum delay amount tdMaxB in this case is smaller than the maximum delay amount tdMaxA when the focus point is closer (FIG. 11A). That is, the difference in the delay amount given between the transducers becomes smaller.

Conventional ultrasound diagnosis apparatuses have a plurality of taps that receives signals output from a plurality of ultrasound transducers, and specify a tap that outputs a signal from each transducer from the delay amount calculated based on the distance between the focus point and each transducer as described above. Therefore, if the difference in the delay amount between the transducers is small, when operating in a configuration in which a fixed amount of delay is assigned to each tap, received signals are concentrated on a specified tap (for example, a tap assigned a small amount of delay) (hereinafter it may be referred to as "tap concentration"). When this tap concentration occurs, received signals are saturated in a circuit receiving signals from the tap on which the signals are concentrated, leading to the possible occurrence of a deteriorated S/N ratio and artifacts.

In order to avoid this saturation of received signals, there is a method of expanding the dynamic range by increasing the power supply voltage and current of the circuit receiving signals from the tap in advance. However, in this case, it is necessary to consider heat generation due to increased power consumption and installation of a fan for inhibiting the heat generation. Therefore, it may result in noise generated by the fan and increased size.

In addition, in conventional ultrasound diagnosis apparatuses, a fixed amount of delay is assigned to each tap, so that the unit of quantization is determined according to the number of taps. Therefore, there is a method of further quantizing the delay amount within one carrier frequency cycle to reduce the tap concentration by increasing the number of taps. However, in this case, circuits are increased with the increased taps, resulting in increased apparatus size and cost.

PRIOR ART DOCUMENT

Patent Document

[Patent Document 1] Japanese Unexamined Patent Application Publication No. 7-124161

SUMMARY OF THE INVENTION

Problems to be Solved by the Invention

The embodiments of the present invention is intended to solve the aforementioned problem, with the intention of preventing saturation of received signals and artifacts from occurring that are associated with tap concentration even if the differences in the delay amount between the transducers are small.

Means for Solving the Problems

In order to achieve the aforementioned object, the embodiments are an ultrasound diagnosis apparatus comprising a plurality of ultrasound transducers, a plurality of taps, a delay amount calculator, a channel distributor, and a delay processor. The plurality of ultrasound transducers transmits ultrasound waves toward a predefined focus point within a subject, and receives reflection waves reflected within the subject. The plurality of taps receives signals output from the plurality of ultrasound transducers. The delay amount calculator calculates a first delay amount per the ultrasound transducer based on the distance between the ultrasound transducer and the focus point. The channel distributor is interposed between the ultrasound transducer and the tap. Moreover, the channel distributor specifies a minimum delay amount and a maximum delay amount from the first delay amount. Further, the channel distributor divides the range from the minimum delay amount to the maximum delay amount by the number of the taps, and relates each of the divided ranges to the tap. Furthermore, the channel distributor inputs signals output from the ultrasound transducer to the tap related to the divided range including the first delay amount corresponding to the ultrasound transducer. The delay processor relates the tap to a previously set second delay amount, and performs delay processing on signals input in each of the taps based on the second delay amount related to the tap.

MODES FOR CARRYING OUT THE INVENTION

[The First Embodiment]

Figure 1:
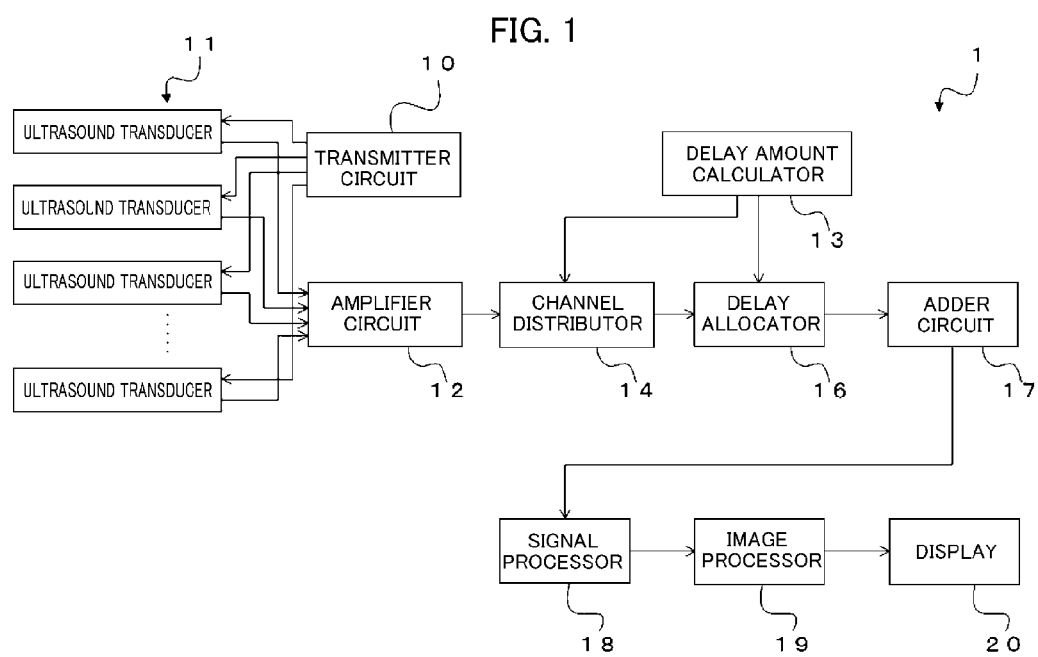
FIG. 1 is a block diagram of an ultrasound diagnosis apparatus according to the present embodiment.

First, the configuration of an ultrasound diagnosis apparatus according to the first embodiment is described with reference to FIG. 1. The block diagram in FIG. 1 shows a configuration of an ultrasound diagnosis apparatus 1 in the ultrasound diagnosis apparatus according to the present embodiment.

The ultrasound diagnosis apparatus 1 is configured to include a transmitter circuit 10, a group of ultrasound transducers 11, an amplifier circuit 12, a delay amount calculator 13, a channel distributor 14, a delay allocator 16, an adder circuit 17, a signal processor 18, an image processor 19, and a display 20.

The transmitter circuit 10 is configured (not shown) to include a clock generator, a frequency divider, a transmit delay circuit, and a pulsar. A clock pulse generated at the clock generator is reduced to, for example, a pulse of around 5 MHz, at the frequency divider. This pulse is provided to the pulsar through the transmit delay circuit to generate a high-frequency voltage pulse which drives (mechanically vibrates) the group of ultrasound transducers 11. Thereby, according to an electric signal from the transmitter circuit 10, an ultrasound beam is irradiated from the group of ultrasound transducers 11 to a subject to be observed.

The group of ultrasound transducers 11 transmits and receives ultrasound waves to and from the subject to be observed (e.g., the heart). The ultrasound beam transmitted from each ultrasound transducer (hereinafter it may be referred to as "each transducer") constituting the group of ultrasound transducers 11 is reflected onto an interface with different acoustic impedance such as the boundary of a structure within the subject to be observed, according to the structure, movement, and the like within the subject.

The ultrasound diagnosis apparatus according to the present embodiment operates in a mode that transmits and receives ultrasound waves by separating the ultrasound waves into a plurality of ultrasound transducers that transmits ultrasound waves and a plurality of ultrasound transducers that receives ultrasound waves. A continuous wave Doppler (hereinafter referred to as "SCW") mode is an example of such a mode.

Figure 2A:
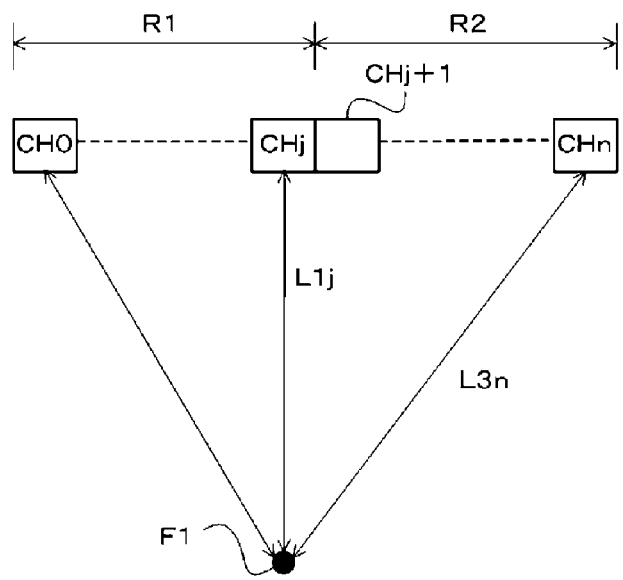
FIG. 2A is a diagram showing a positional relationship between a focus point and each transducer in the ultrasound diagnosis apparatus according to the first embodiment.

Now refer to FIG. 2A. FIG. 2A shows a positional relationship between transducers CH0-CHn comprising the group of ultrasound transducers 11 and a focus point F1. If the ultrasound diagnosis apparatus operates in the SCW mode, as shown in FIG. 2A, the apparatus separates the group of ultrasound transducers 11 into a region R2 that transmits ultrasound waves (transducers CHj+1-CHn) and a region R1 that receives ultrasound waves (transducers CH0-CHj). In addition, hereinafter, it is described such that each transducer (CH0-CHj) and the focus point F1 are in the positional relationship shown in FIG. 2A. Moreover, if a particular transducer is indicated, the symbol indicating the transducer is attached, and if no particular transducer is specified, a "transducer" is simply described without any symbol.

Figure 3:
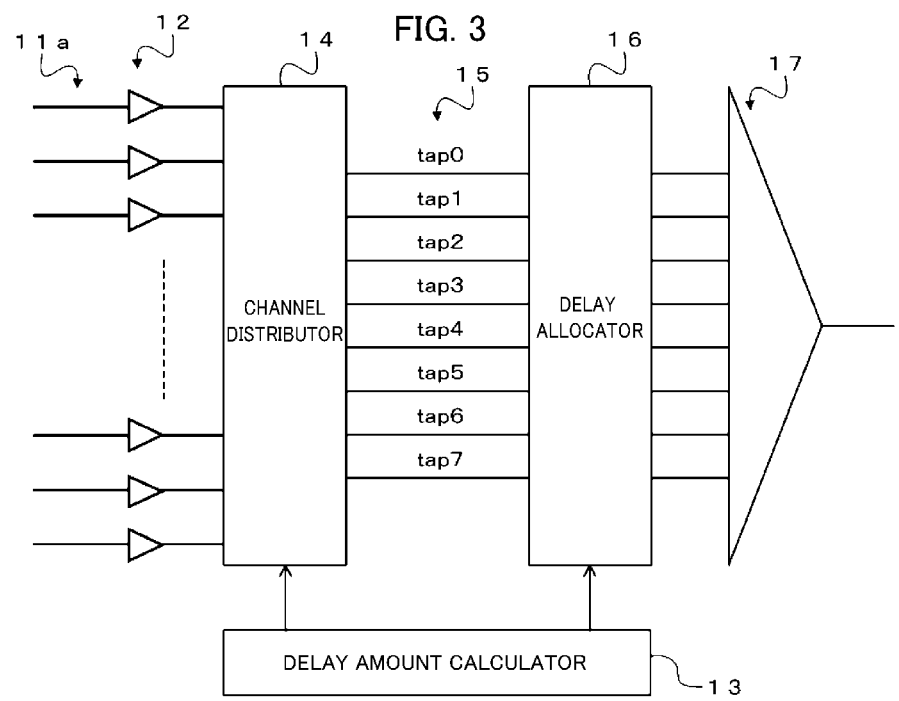
FIG. 3 is a block diagram of a section that phases and adds received signals in the ultrasound diagnosis apparatus according to the present embodiment.

Now refer to FIG. 3. FIG. 3 is a block diagram describing a configuration to phase and add received signals, that is, a detailed configuration including the amplifier circuit 12, the delay amount calculator 13, the channel distributor 14, the delay allocator 16, and the adder circuit 17. As shown in FIG. 3, taps 15 (tap0-tap7) are interposed between the channel distributor 14 and the delay allocator 16. That is, output from the channel distributor 14 is input to a tap 15, and then output from the tap 15 to the delay allocator 16. Details of each configuration are described below.

The amplifier circuit 12 receives ultrasonic echo signals received at each transducer via a signal line 11a connected to each transducer of the group of ultrasound transducers 11. The amplifier circuit 12 conducts processing such as low noise amplification and buffering in order to better transmit the ultrasonic echo signals received from each transducer.

The delay amount calculator 13 calculates a delay amount based on the distance between the focus point F1 and each transducer (CH0-CHn). The delay amount calculator 13 outputs the calculated delay amount to the channel distributor 14 and the delay allocator 16. The channel distributor 14 and the delay allocator 16 are described later. In addition, the delay amount calculated by the delay amount calculator 13 corresponds to a "first delay amount."

The channel distributor 14 receives the delay amount corresponding to each transducer from the delay amount calculator 13. The channel distributor 14 specifies a maximum delay amount, which is the maximum value, from the delay amount corresponding to each transducer (CH0-CHj) in the region R1 that receives ultrasound waves. The channel distributor 14 calculates a time duration tD1yRange from the delay amount 0 to the maximum delay amount.

Next, the channel distributor 14 compares the time duration tD1yRange with a cycle Tc of the ultrasound waves. If the time duration tD1yRange is more than the cycle Tc of the ultrasound waves, the channel distributor 14 divides the cycle Tc into ranges by the number of taps 15 in advance, and then relates this range to each tap. The operation in this case is similar to that of conventional ultrasound diagnosis apparatuses. Moreover, if the time duration tD1yRange is less than the cycle Tc of the ultrasound waves, the channel distributor 14 divides the time duration tD1yRange by the number of taps 15, and then relates the divided range to each tap. The channel distributor 14 inputs the output from the transducer related to the delay amount included in the divided range to the tap related to the divided range.

Figure 2B:
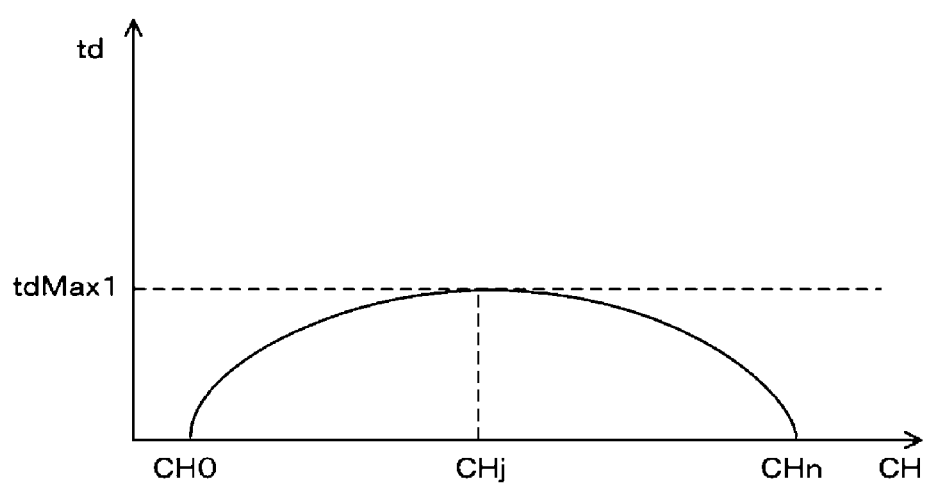
FIG. 2B is a diagram showing a relationship with a delay amount to provide to each transducer in the ultrasound diagnosis apparatus according to the first embodiment.
Figure 4:
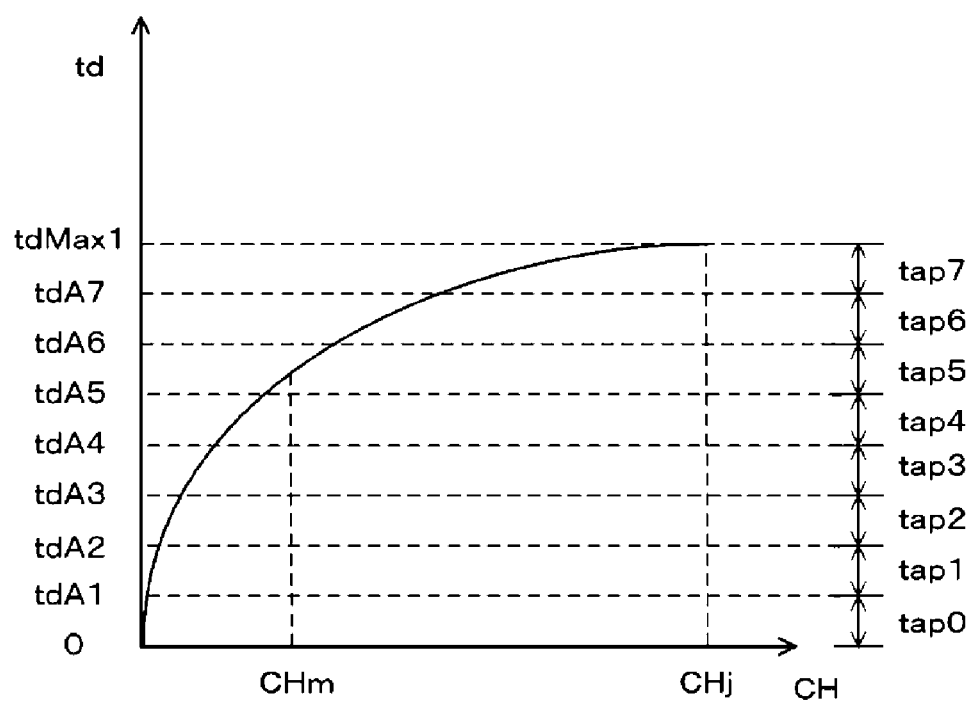
FIG. 4 is a diagram describing distribution of received signals to each tap in the ultrasound diagnosis apparatus according to the first embodiment.

Hereinafter, it is specifically described with reference to FIG. 2B and FIG. 4 that dividing the delay amount and relating the delay amount to each tap by the channel distributor 14, when the time duration tD1yRange is less than the cycle Tc of the ultrasound waves. FIG. 2B is a graph of the delay amount corresponding to each transducer, which has been calculated based on the distance between the focus point F1 and each transducer in the positional relationship between the focus point F1 and the transducers CH0-CHn shown in FIG. 2A. In FIG. 2B, the horizontal axis corresponds to each transducer CH while the vertical axis corresponds to the delay amount td. Moreover, FIG. 4 is a diagram describing division of the delay amount and the distribution of received signals to each tap by the channel distributor 14, showing a portion corresponding to each transducer (CH0-CHj) in the region R1 that receives ultrasound waves from FIG. 2B. In FIG. 4, the horizontal axis corresponds to each transducer CH while the vertical axis corresponds to the delay amount td.

If the focus point F1 is in the position shown in FIG. 2A, a distance L1j from the focus point F1 to the transducer CHj is the farthest. Therefore, as shown in FIG. 2B, the delay amount corresponding to the transducer CHj is the largest. The delay amount in this transducer CHj corresponds to a maximum delay amount tdMax1.

Now refer to FIG. 4. The channel distributor 14 divides the time duration tD1yRange, i.e., the time duration of the delay amount 0-tdMax 1, into ranges of the number of taps "8" (tap0-tap7), i.e., 8 ranges defined as 0, tdA1-tdA7, and tdMax1. The channel distributor 14 assigns each of the divided ranges to each tap (tap0-tap7). That is, the channel distributor 14 assigns the range indicated by 0-tdA1 to tap0, and the range indicated by tdA1-tdA2 to tap1. In a similar manner, each range within tdA2-tdMax1 is also assigned to tap2-tap7, respectively. In addition, if the time duration tD1yRange is more than the cycle Tc of the ultrasound waves, each range in which the cycle Tc is divided into the number of taps is assigned to tap0-tap7.

Next, the channel distributor 14 inputs the output from each transducer (CH0-CHj) to the tap related to the delay amount included in each range. For example, in the case of the example shown in FIG. 4, the delay amount related to the transducer CHj is included in the range tdA7-tdMax1. Therefore, the channel distributor 14 inputs the output from the transducer CHj to tap7 related to the range tdA7-tdMax1. Similarly, the delay amount related to the transducer CHm is included in the range tdA5-tdA6. Therefore, the channel distributor 14 inputs the output from the transducer CHm to tap5 related to the range tdA5-tdA6. In this way, the channel distributor 14 relates the transducer to each tap, and inputs the output from each transducer to the corresponding tap. In addition, the channel distributor 14 may be configured with a multiplexer or a matrix switch, for example. Moreover, the tap 15 may be able to distribute signals from each transducer to the types of the number of taps. Therefore, the tap 15 may be provided with terminals corresponding to tap0-tap7, and configured to receive separate signals, or configured to distribute each signal with wiring.

The delay allocator 16 is configured to be capable of selecting the delay amount at which the delay amount in one cycle of the ultrasound waves (in one carrier frequency cycle) is quantized by the number of quantized "16" (hereinafter referred to as "quantized delay amount"). This is because it is not necessary to provide a time difference corresponding to a channel difference, since, in the continuous wave Doppler mode, the same phase information is repeated for each waveform of received ultrasound waves (there is periodicity of the waveform). In addition, "quantization" means converting the delay amount corresponding to each transducer, which is an analog value, into a discrete approximation, i.e., a quantized delay amount. Moreover, this quantized delay amount corresponds to a "second delay amount." The delay allocator 16 relates this quantized delay amount to each tap, and conducts delay processing on the output from the tap with the quantized delay amount related to that tap. This operation of the delay allocator 16 is specifically described below.

Figure 5:
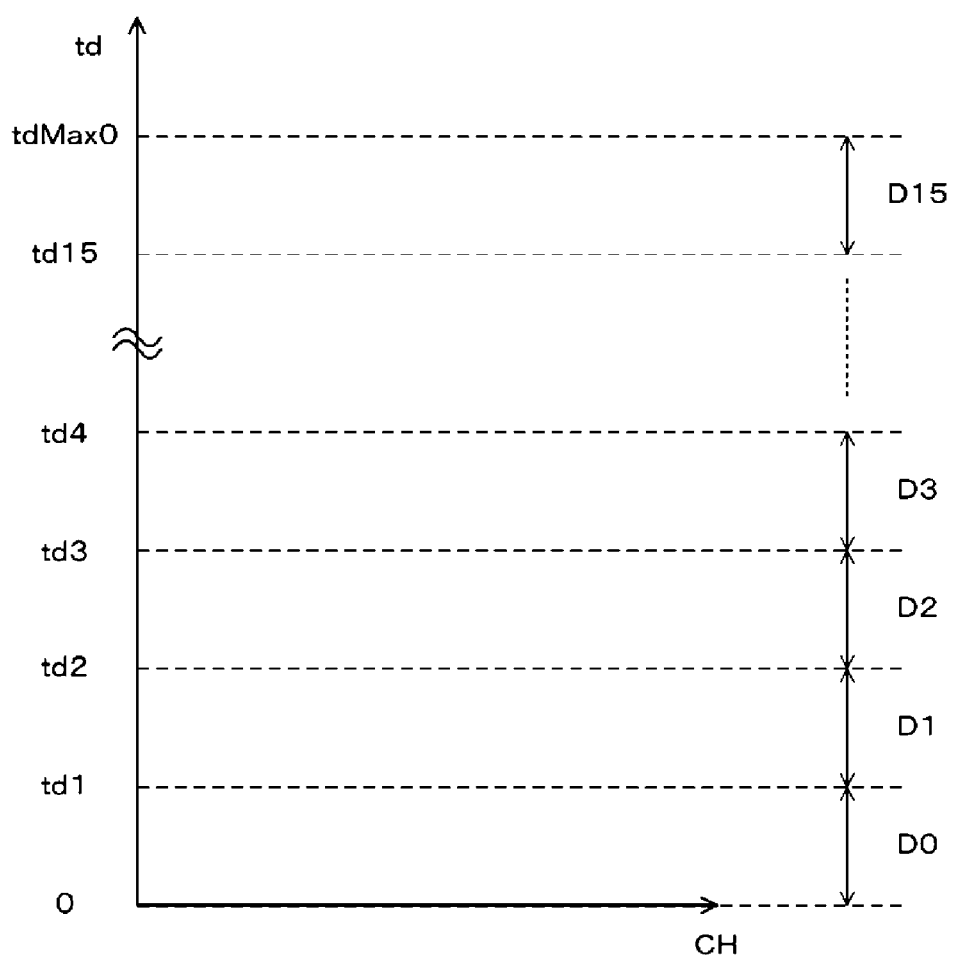
FIG. 5 is a diagram describing quantization of the delay amount in the present embodiment.

First, quantization of the delay amount by the delay allocator 16 is specifically described with reference to FIG. 5. FIG. 5 is a graph with the vertical axis being related to the delay amount td and the horizontal axis to each transducer CH. tdMax0 in FIG. 5 indicates the maximum delay amount from the delay amount in one carrier frequency cycle. The delay allocator 16 divides the delay amount O-tdMax0 into ranges of the quantization number "16," i.e., "16" ranges defined as 0, td1-td15, and tdMax0. The width of each range after this division is the quantizing interval. In addition, in the description of the present embodiment, although the quantization number is described as "16," the quantization number of the delay amount is preferably 8 or more, and not limited to "16." This is because it is known that the divergence of the main beam will be 10% or less compared to the case without quantization of delay (continuous delay) if the accuracy of delay quantization has a roughness below "$\lambda/8$" of the carrier signal. That is, it is known that sensitivity degradation due to the divergence of the beam can be held within "−1 dB" by defining the quantization number of the delay amount as 8 or more. Moreover, as the details are described later, the quantization number of the delay amount is preferably larger than the number of taps.

The delay allocator 16 quantizes the delay amount for one carrier frequency cycle with the quantization number "16" based on this quantizing interval. For example, the range indicated by 0-td1 is assigned to a quantized delay amount D0 while the range indicated by td1-td2 is assigned to a quantized delay amount D1. Similarly, each range within td2-tdMax0 is also assigned to quantized delay amount D2-D15. In addition, hereinafter, from the range of the delay amount, the range related to the quantized delay amount D0-D15 may be referred to as a "quantized range."

The delay allocator 16 specifies a representative value for the delay amount from the range of each delay amount related to tap0-tap7. As an example, the delay allocator 16 specifies the central value in the range of the delay amount as the representative value for the delay amount. For example, in the case of tap1, the representative value for the delay amount is (tdA2-tdA1)/2. The delay allocator 16 converts the representative value for the delay amount specified per tap into the delay amount in one cycle of the ultrasound waves to define the representative value as a representative delay amount $td_{tap0}$-$td_{tap7}$. Next, the delay allocator 16 compares the calculated representative delay amount $td_{tap0}$-$td_{tap7}$ with each quantization range corresponding to the quantized delay amount D0-D15. In addition, the delay allocator 16, similar to the channel distributor 14, may be configured to receive the delay amount corresponding to each transducer from the delay amount calculator 13 and calculate the representative delay amount $td_{tap0}$-$td_{tap7}$. The delay allocator 16 may also be configured to obtain the representative delay amount $td_{tap0}$-$td_{tap7}$ from the channel distributor 14. Further, the representative value for the delay amount may be a value included in the range of the delay amount, and not be limited to the central value. For example, the minimum value in the range of the delay amount may be the representative value, or the maximum value may be the representative value.

Figure 6:
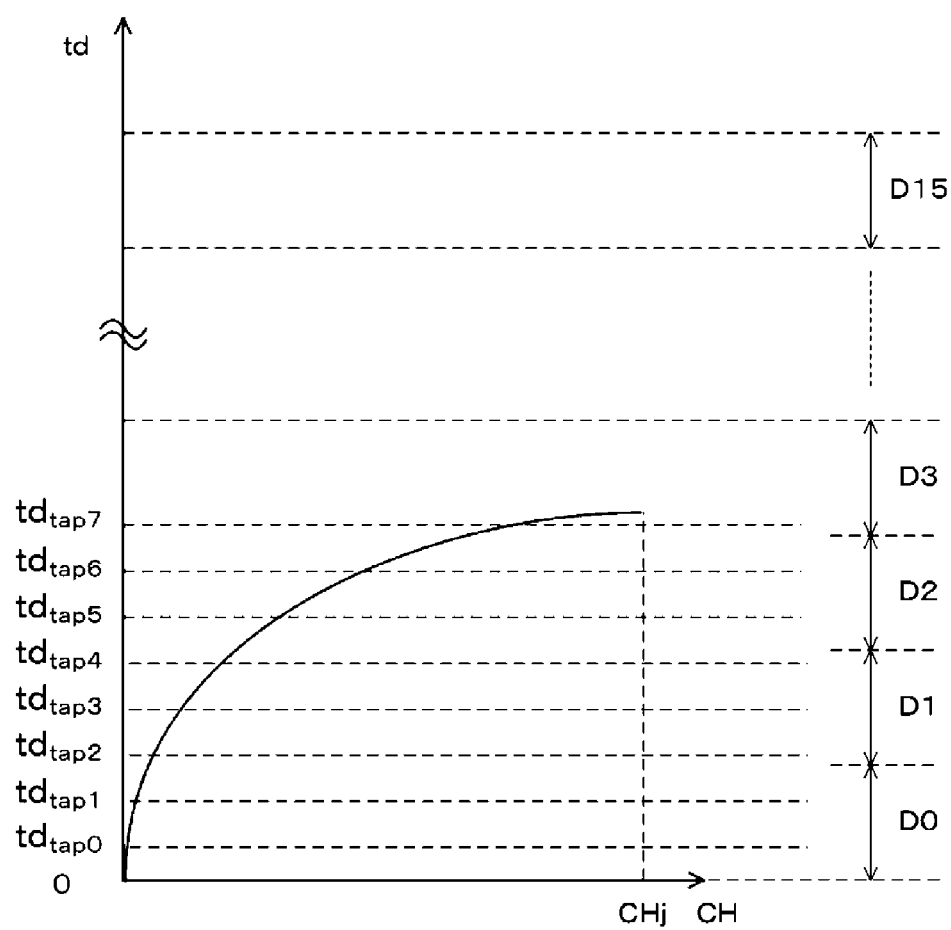
FIG. 6 is a diagram describing allocation of the quantized delay amount to each tap in the ultrasound diagnosis apparatus according to the first embodiment.

The delay allocator 16 checks whether the representative delay amount $td_{tap0}$-$td_{tap7}$ related to each tap is included in any of respective quantization ranges based on the comparison result. The delay allocator 16 relates the output from each tap to the quantized delay amount (D0-D15) related to the quantization range including the representative delay amount ($td_{tap0}$-$td_{tap7}$) corresponding to that tap. This operation of the delay allocator 16 is described with reference to FIG. 6. FIG. 6 is a graph describing the allocation of the quantized delay amount to each tap by the delay allocator 16, and shows a relationship between the representative delay amount ($td_{tap0}$-$td_{tap7}$) and the quantized delay amount (D0-D15). In FIG. 6, the horizontal axis corresponds to each transducer CH, while the vertical axis corresponds to the delay amount td.

For example, the output from tap0 corresponds to the representative delay amount $td_{tap0}$, and $td_{tap0}$ is included in the quantization range corresponding to the quantized delay amount D0. In this case, the delay allocator 16 relates the output from tap0 to the quantized delay amount D0. The delay allocator 16 also relates tap1-tap7 to the quantized delay amount in a similar manner to tap0. That is, the delay allocator 16 relates tap0 and tap1 to the quantized delay amount D0, tap2-tap4 to the quantized delay amount D1, tap5 and tap6 to the quantized delay amount D2, and tap7 to the quantized delay amount D3.

The delay allocator 16 performs delay processing on the output from each tap based on the related quantized delay amount. For example, in the case of analog delay, the delay allocator 16 may switch to connect the output from each tap to a delay line corresponding to the quantized delay amount. Such as a matrix switch, for example, can be used for this switching. Also, in the case of digital delay, the configuration to perform delay processing in the delay allocator 16 may be replaced with a digital beam former unit, for example, as appropriate. In this way, the output from each tap is output to the related delay circuit (delay line or digital beam former unit). Therefore, the delay quantization number is preferably kept larger than the number of taps. Specifically, keeping the delay quantization number larger than the number of taps makes it possible to reduce the output concentration on a particular circuit (e.g., delay circuit) more than when operating in a configuration of assigning a fixed delay amount to each tap. In addition, the delay allocator 16 outputs the output from each tap treated with delay processing to the adder circuit 17.

The adder circuit 17 adds a received signal treated with delay processing for each tap at the delay allocator 16. This amplifies the received signal, and improves the S/N ratio of the received signal.

The signal processor 18 receives the received signal amplified at the adder circuit 17. The signal processor 18 extracts a signal reflected by fluid within a subject to be observed, by performing quadrature detection on the received signal, converting the signal into a baseband signal, and then passing the signal through a high-pass filter. The signal processor 18 extracts a Doppler shift frequency component by performing antialiasing on the extracted signal, converting the signal into a digital signal with an A/D converter, and then performing frequency analysis. The signal processor 18 calculates the velocity of a movable object (e.g., blood) within the subject based on this Doppler shift frequency component. The image processor 19 receives the calculated velocity of the movable object, and generates a screen in which the calculated velocity is visibly displayed, like a graph with the horizontal axis as time and the vertical axis as velocity. The image processor 19 causes the generated screen to be displayed on the display 20.

(A Series of Operations)

Figure 7:
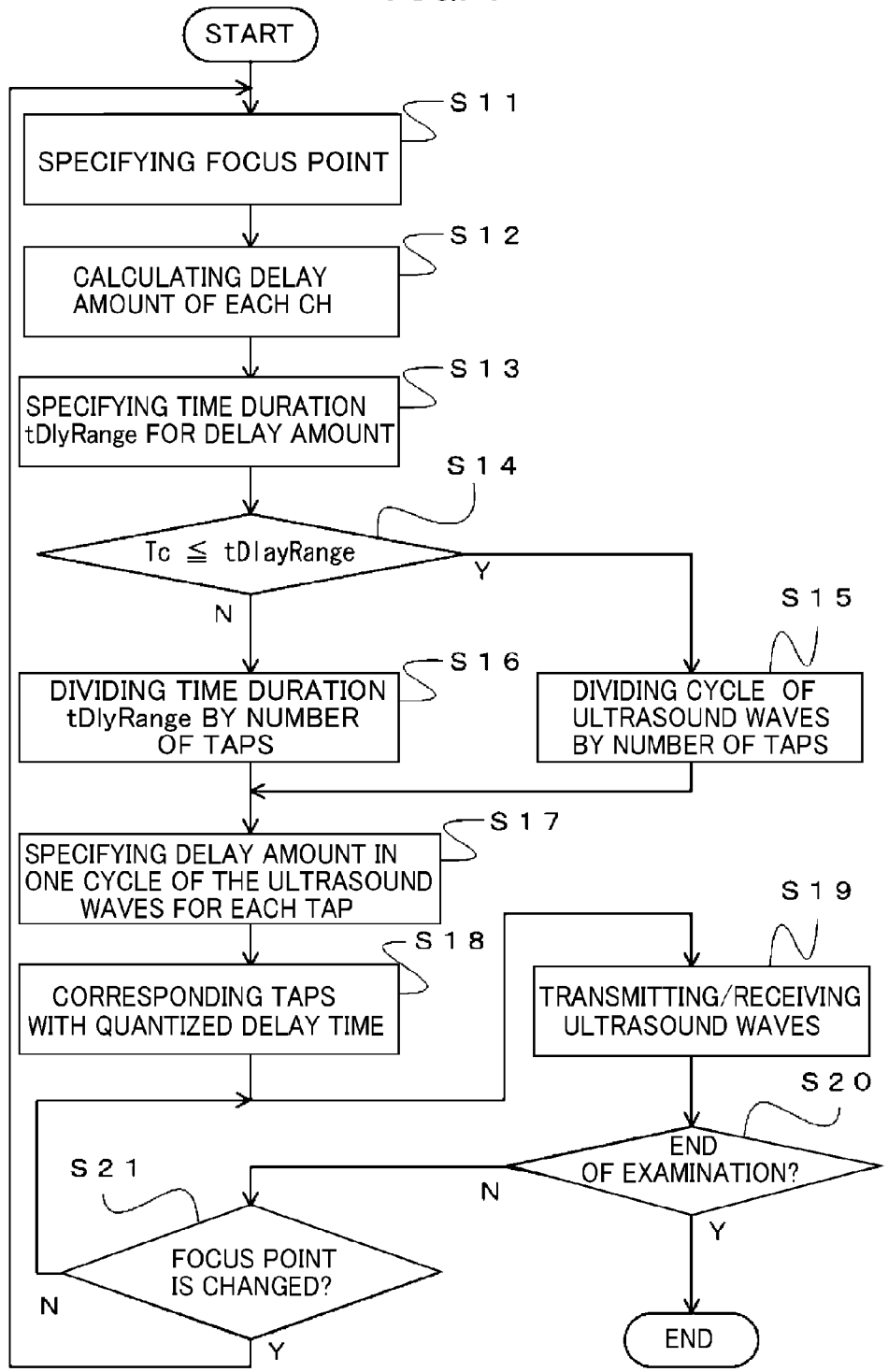
FIG. 7 is a flowchart showing a series of processing flows for the ultrasound diagnosis apparatus according to the present embodiment.

Next, a series of operations of the ultrasound diagnosis apparatus according to the present embodiment is described with reference to FIG. 7. FIG. 7 is a flowchart showing a series of processing flows for the ultrasound diagnosis apparatus according to the present embodiment.

(Step S11)

When the ultrasound diagnosis apparatus is activated by turning on its power, the delay amount calculator 13 of the ultrasound diagnosis apparatus first receives the designation of the focus point receiving continuous wave Doppler from an operator, and specifies the position of the focus point in a subject. As described later, the focus point and each transducer are in the positional relationship shown in FIG. 2A.

(Step S12)

The delay amount calculator 13 calculates the delay amount corresponding to each transducer based on the distance between the specified focus point F1 and each transducer CH0-CHn. The delay amount calculator 13 then outputs the calculated delay amount corresponding to each transducer to the channel distributor 14 and the delay allocator 16.

(Step S13)

The channel distributor 14 specifies, from the delay amount corresponding to each transducer received from the delay amount calculator 13, the maximum delay amount tdMax1, in which the delay amount is the maximum from the delay amount corresponding to each transducer (CH0-CHj) in the region R1 that receives ultrasound waves. Moreover, the channel distributor 14 calculates the time duration tD1yRange from the delay amount 0 to the maximum delay amount tdMax1.

(Step S14)

Next, the channel distributor 14 compares the time duration tD1yRange with the cycle Tc of the ultrasound waves.

(Step S15)

If the time duration tD1yRange is more than the cycle Tc of the ultrasound waves (Step S14, Y), the channel distributor 14 divides the cycle Tc into ranges by the number of taps 15 in advance, and then relates these ranges to each tap. The channel distributor 14 inputs the output from the transducer related to the delay amount included in each range to the tap related to the range.

(Step S16)

Moreover, if the time duration tD1yRange is less than the cycle Tc of the ultrasound waves (Step S14, N), the channel distributor 14 divides the time duration tD1yRange by the number of taps 15 "8," and assigns these divided ranges to each tap (tap0-tap7). Thereby, the time duration represented by the delay amount 0-tdMax1 is divided into 8 ranges defined as the delay amount 0, tdA1-tdA7, and tdMax1, and these ranges are related to respective taps. The channel distributor 14 inputs the output from the transducer related to the delay amount included in each range to the tap related to the range.

(Step S17)

Next, the delay allocator 16 specifies a representative value for the delay amount from the range of each delay amount related to tap0-tap7. As an example, the delay allocator 16 specifies the central value in the range of the delay amount as the representative value for the delay amount. For example, in the case of tap1, the representative value for the delay amount is (tdA2-tdA1)/2. The delay allocator 16 converts the representative value for the delay amount specified for each tap into the delay amount in one cycle of the ultrasound waves to define the delay amount as a representative delay amount $td_{tap0}$-$td_{tap7}$.

(Step S18)

The delay allocator 16 compares the representative delay amount $td_{tap0}$-$td_{tap7}$ corresponding to each tap with each quantization range corresponding to the quantized delay amount D0-D15 in which the delay amount for one carrier frequency cycle has been quantized. The delay allocator 16 checks whether the representative delay amount $td_{tap0}$-$td_{tap7}$ related to each tap is included in any of the respective quantization ranges based on the comparison result. The delay allocator 16 relates the output from each tap to the quantized delay amount (D0-D15) related to the quantization range including the representative delay amount ($td_{tap0}$-$td_{tap7}$) corresponding to that tap. Thereby, the delay allocator 16, as shown in FIG. 6, for example, relates tap0 and tap1 to the quantized delay amount D0, tap2-tap4 to the quantized delay amount D1, tap5 and tap6 to the quantized delay amount D2, and tap7 to the quantized delay amount D3.

(Step S19)

Next, a controller (not shown) controls, among the group of ultrasound transducers 11, each transducer (CHj+1-CHn) in the region R2 that transmits ultrasound waves, and then transmits the ultrasound waves to the subject. The ultrasound waves reflected within the subject is received by each transducer (CH0-CHj) in the region R1 that receives ultrasound waves in the group of ultrasound transducers 11. The ultrasound echo signal received by each transducer (CH0-CHj) in the region R1 is amplified by the amplifier circuit 12, and input to each tap that has been related by the channel distributor 14.

Next, the delay allocator 16 performs delay processing on the output from each tap based on the related quantized delay amount. The delay allocator 16 outputs the output from each tap treated with the delay processing to the adder circuit 17. The adder circuit 17 adds a received signal from the delay allocator 16 for each tap, and then outputs the resultant signal to the signal processor 18. The signal processor 18 receives the signal output from the adder circuit 17, and then calculates the velocity of the movable object in the subject. The image processor 19 receives the calculated velocity of the movable object, generates a screen on which the calculated velocity is visibly displayed, and displays the screen the on the display 20.

(Step S21)

The ultrasound examination is continued until the end of the examination is instructed by the operator (Step S20, N). If the position of the focus point is changed (Step S21, Y) upon the operation by the operator during the ultrasound examination, processing according to Steps S11-S18 is executed again, and processing related to the examination (Step S19) is then performed. If the position of the focus point is not changed (Step S21, N), processing related to the examination (Step S19) continues to be executed.

(Step S20)

When the end of the ultrasound examination is instructed by the operator (Step S20, Y), processing related to the ultrasound examination is finished.

In addition, although the number of taps is described as "8" and the quantization number of the delay amount by the delay allocator 16 as "16" above, the numbers are not necessarily limited to these. The delay quantization number and the number of taps may be changed as appropriate depending on the performance of the ultrasound diagnosis apparatus, though a configuration to set the delay quantization number to be larger than the number of taps is more preferable.

As described above, with the ultrasound diagnosis apparatus according to the present embodiment, as in the case that the depth of the focus point is deep, all the taps are used even if the difference in the delay amount between the transducers is small. Therefore, it is possible to reduce the concentration of signals on a particular tap, making it possible to prevent saturation of received signals and artifacts from occurring that are associated with tap concentration. Moreover, it is no longer necessary to assign a fixed amount of delay to each tap as in conventional ultrasound diagnosis apparatuses. Therefore, it is possible to set the quantization number of the delay amount without depending on the number of taps. Moreover, because it is not necessary to increase the number of taps, it is possible to prevent tap concentration while inhibiting any increase in power consumption, size, and cost.

[The Second Embodiment]

The channel distributor 14 according to the first embodiment specified the maximum delay amount and divided the time duration from the delay amount 0 to the maximum delay amount into the ranges of the number of taps (tap0-tap7). A channel distributor 14 according to the second embodiment is different from the former in that the distributor 14 further specifies, in addition to the maximum delay amount, the minimum delay amount in which the delay amount is minimum, and divides the time duration from the minimum delay amount to the maximum delay amount into the ranges of the number of taps (tap0-tap7).

Figure 8A:
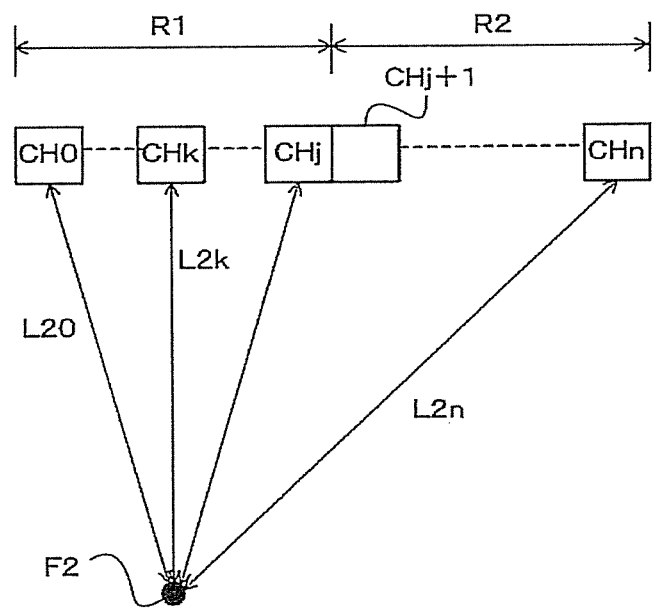
FIG. 8A is a diagram showing a positional relationship between a focus point and each transducer in an ultrasound diagnosis apparatus according to the second embodiment.

First refer to FIG. 8A. FIG. 8A shows a positional relationship between the transducers CH0-CHn comprising the group of ultrasound transducers 11 and a focus point F2. As shown in FIG. 8A, the focus point F2 is located on the side of the region R1 that receives ultrasound waves rather than in the center of the group of ultrasound transducers 11. In addition, in this case, a distance L2k between a transducer CHk included in the region R1 and the focus point F2 is the closest, while a distance L2 n between the transducer CHn included in the region R2 that transmits ultrasound waves and the focus point F2 is the farthest.

Figure 8B:
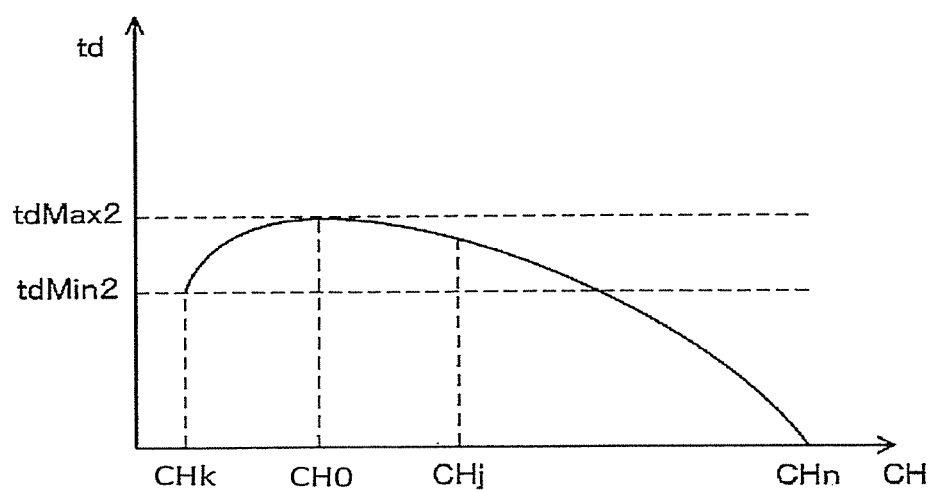
FIG. 8B is a diagram showing a relationship with a delay amount to provide to each transducer in the ultrasound diagnosis apparatus according to the second embodiment.

Now refer to FIG. 8B. FIG. 8B is a diagram showing the delay amount corresponding to each transducer calculated based on the distance between the focus point F2 and each transducer in the positional relationship between the focus point F2 and the transducers CH0-CHn shown in FIG. 8A. In FIG. 8B, the horizontal axis corresponds to each transducer CH, while the vertical axis corresponds to the delay amount td. The delay amount related to each transducer is calculated based on the distance L2 n between the transducer CHn and the focus point F2. In this case, as shown in FIG. 8B, the minimum value for the delay amount related to each transducer in the region R1 that receives ultrasound waves is a delay amount tdMin2 corresponding to the transducer CH0. Therefore, the delay amount within the delay amount 0-tdMin2 related to each transducer in the region R2 that transmits ultrasound waves is not used for delay processing of received signals. Thus, even though this range is quantized and assigned to a tap, the received signals are not input to the tap, and are concentrated on other taps.

In response to this, the channel distributor 14 according to the present embodiment specifies the minimum delay amount tdMin2 in addition to a maximum delay amount tdMax2, and divides the time duration from the delay amount tdMin2 to tdMax2 into the range of the number of taps (tap0-tap7). Thereby, as shown in FIG. 8B, also for the case in which there is a delay amount not used for delay processing among the calculated delay amount for each transducer, the tap is thoroughly used the taps in the range of the delay amount used for delay processing. The configuration of the channel distributor 14 that is different from the ultrasound diagnosis apparatus according to the first embodiment is particularly described below.

The channel distributor 14 receives the delay amount corresponding to each transducer from the delay amount calculator 13. This amount of delay corresponding to each transducer is calculated by the delay amount calculator 13 based on the distance between the focus point F2 and each transducer (CH0-CHn). The channel distributor 14 specifies the maximum delay amount and the minimum delay amount from the delay amount corresponding to each transducer (CH0-CHj) in the region R1 that receives ultrasound waves.

The channel distributor 14 calculates the time duration tD1yRange from the specified minimum delay amount to the maximum delay amount.

Figure 9A:
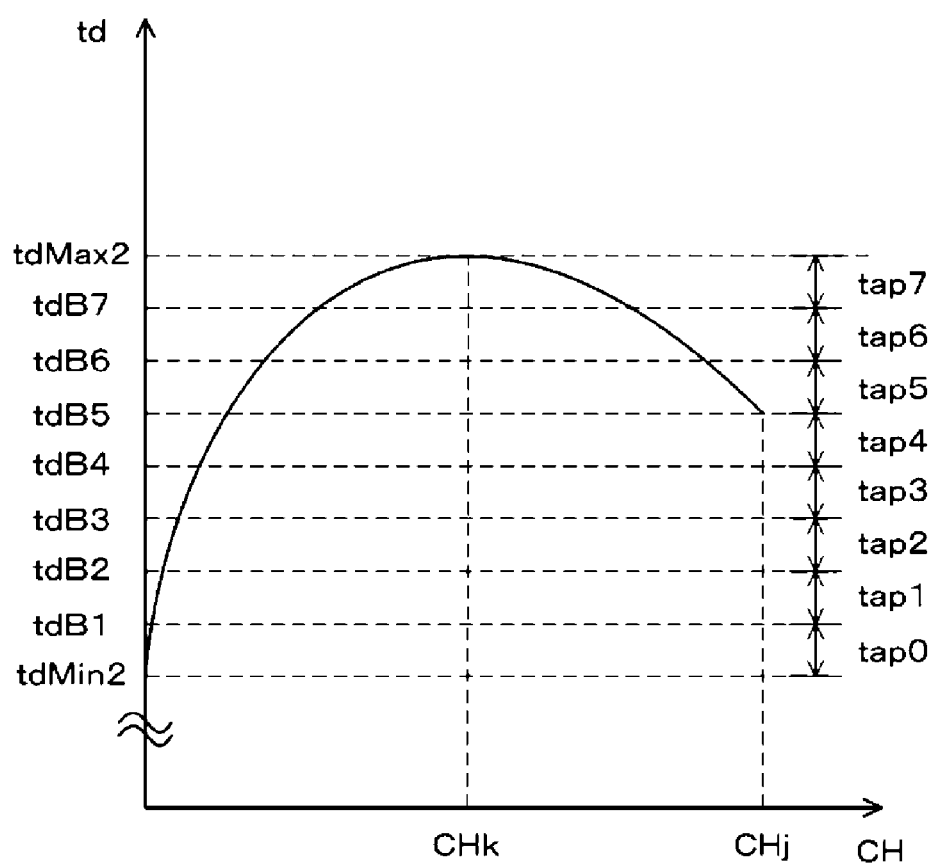
FIG. 9A is a diagram describing a distribution of received signals to each tap in the ultrasound diagnosis apparatus according to the second embodiment.
Figure 9B:
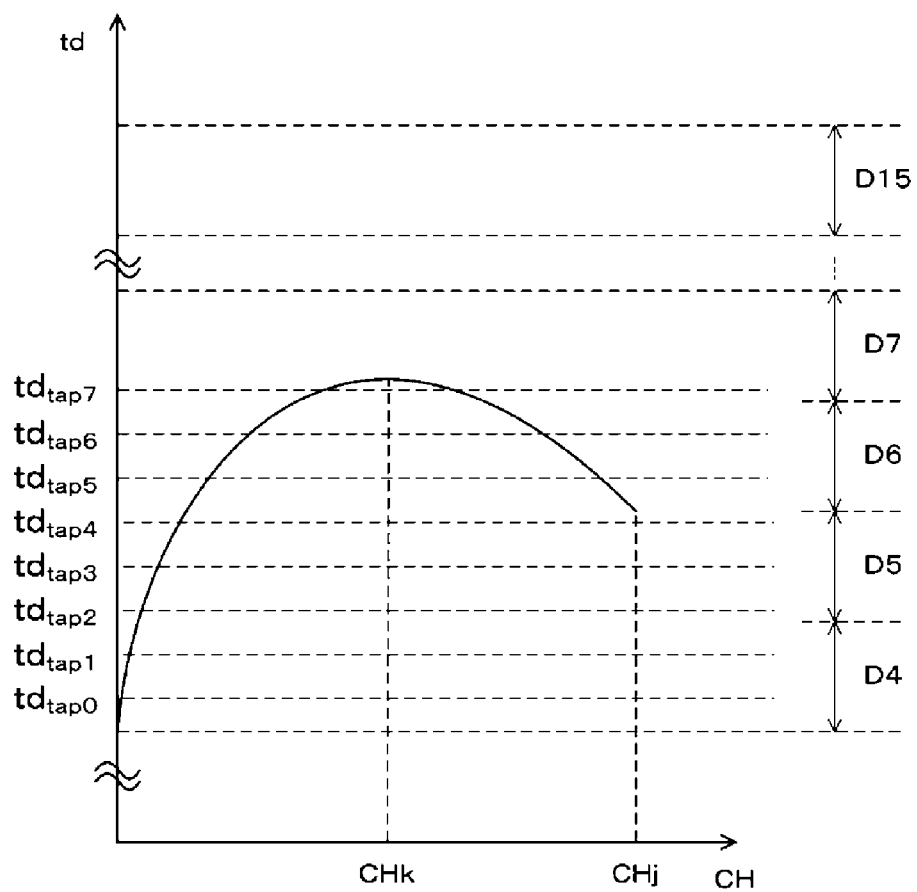
FIG. 9B is a diagram describing allocation of a quantized delay amount to each tap in the ultrasound diagnosis apparatus according to the second embodiment.

Next, the channel distributor 14 compares the time duration tD1yRange with the cycle Tc of the ultrasound waves. If the time duration tD1yRange is more than the cycle Tc of the ultrasound waves, the channel distributor 14 divides the cycle Tc into ranges by the number of taps 15 in advance, and relates this range to each tap. The operation in this case is similar to that of the ultrasound diagnosis apparatus according to the first embodiment. Moreover, if the time duration tD1yRange is less than the cycle Tc of the ultrasound waves, the channel distributor 14 divides the time duration tD1yRange by the number of taps 15, and relates the divided range to each tap Hereinafter, it is specifically described with reference to FIG. 8B, FIG. 9A and FIG. 9B that dividing the delay amount and relating the delay amount to each tap by the channel distributor 14, when the time duration tD1yRange is less than the cycle Tc of the ultrasound waves. FIG. 9A is a diagram describing the division of the delay amount and the distribution of received signals to each tap by the channel distributor 14. FIG. 9A shows a portion corresponding to each transducer (CH0-CHj) in the region R1 that receives ultrasound waves in FIG. 8B. Moreover, FIG. 9B is a graph describing allocation of the quantized delay amount to each tap by the delay allocator 16. In addition, in FIG. 9A and FIG. 9B, the horizontal axis corresponds to each transducer CH, while the vertical axis corresponds to the delay amount td.

If the focus point F2 is in the position shown in FIG. 8A, a distance L20 from the focus point F2 to the transducer CH0 is the farthest. Therefore, as shown in FIG. 8B, the delay amount corresponding to the transducer CH0 is the largest. This delay amount in the transducer CH0 corresponds to the maximum delay amount tdMax2. Moreover, among the transducers CH0-CHj included in the region R1, a distance L2k to the transducer CHk is the closest. Therefore, as shown in FIG. 8B, the delay amount corresponding to the transducer CHk is the smallest. This delay amount in the transducer CHk corresponds to the minimum delay amount tdMin2.

Now refer to FIG. 9A. The channel distributor 14, as shown in FIG. 9A, divides the time duration tD1yRange, i.e., the time duration of the delay amount tdMin2-tdMax2, into ranges of the number of taps "8" (tap0-tap7), i.e., 8 ranges defined as tdMin2, tdB1-tdB7, and tdMax2. The channel distributor 14 assigns these divided ranges to each tap (tap0-tap7). That is, the channel distributor 14 assigns the range defined as tdMin2-tdB1 to tap0, and the range indicated by tdB1-tdB2 to tap 1, . . . , the range indicated by tdAB-tdB7 to tap6, and the range tdB7-tdMax2 to tap7. In addition, if the time duration tD1yRange is more than the cycle Tc of the ultrasound waves, each range in which the cycle Tc is divided into the number of taps is assigned to tap0-tap7.

Next, the channel distributor 14 inputs the output from the transducer related to the delay amount included in each range to the tap related to that range. For example, the delay amount related to the transducer CHj is included in the range tdB5-tdB6. Therefore, the channel distributor 14 inputs the output from the transducer CHj to tap5 related to the range tdB5-tdB6. Similarly, the delay amount related to the transducer CHk is included in the range tdB7-tdMax2. Therefore, the channel distributor 14 inputs the output from the transducer CHk to tap7 related to the range tdB7-tdMax2. In this way, the channel distributor 14 relates the transducer to each tap, and inputs the output from each transducer to the corresponding tap.

The following operations are similar to that of the ultrasound diagnosis apparatus according to the first embodiment. Namely, the delay allocator 16 specifies a representative delay amount $td_{tap0}$-$td_{tap7}$ from each range of the delay amount related to tap0-tap7. Next, the delay allocator 16, as shown in FIG. 9B, compares the representative delay amount $td_{tap0}$-$td_{tap7}$ corresponding to each tap with each quantization range corresponding to the quantized delay amount D0-D15. The delay allocator 16, based on the comparison result, relates the output from each tap to the quantized delay amount (D0-D15) related to the quantization range including the representative delay amount ($td_{tap0}$-$td_{tap7}$) corresponding to that tap. Thereby, the delay allocator 16 relates tap0 and tap1 to the quantized delay amount D4, tap2-tap4 to the quantized delay amount D5, tap5 and tap6 to the quantized delay amount D6, and tap7 to the quantized delay amount D7. The delay allocator 16 performs delay processing on the output from each tap based on the related quantized delay amount, and outputs each output treated with this delay to the adder circuit 17. The adder circuit 17 adds a received signal given the delay amount for each tap by the delay allocator 16, and outputs the resultant signal to the signal processor 18.

Figure 10A:
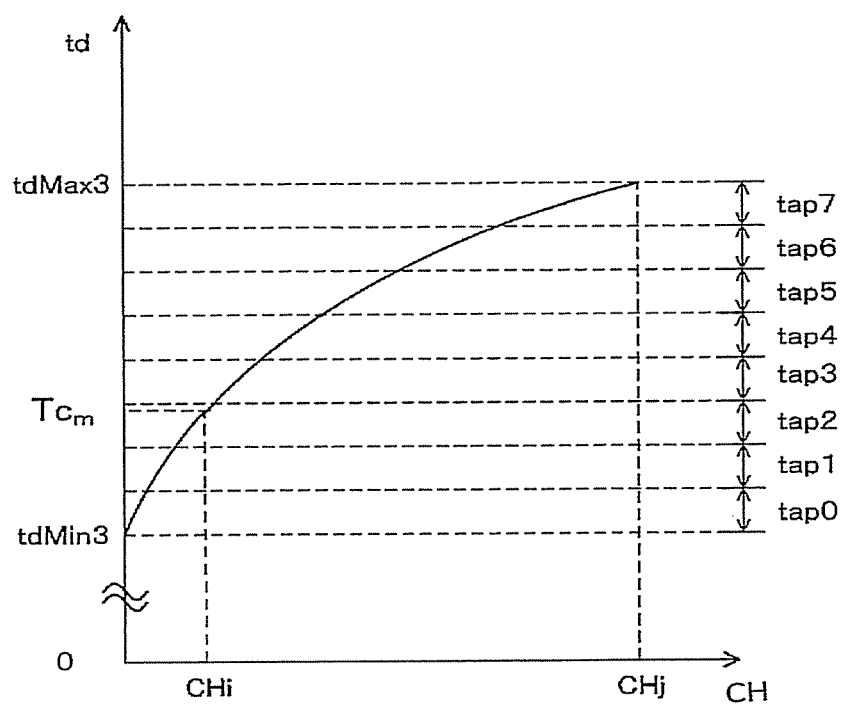
FIG. 10A is an example of a correspondence relationship between a divided amount of delay and each tap.
Figure 10B:
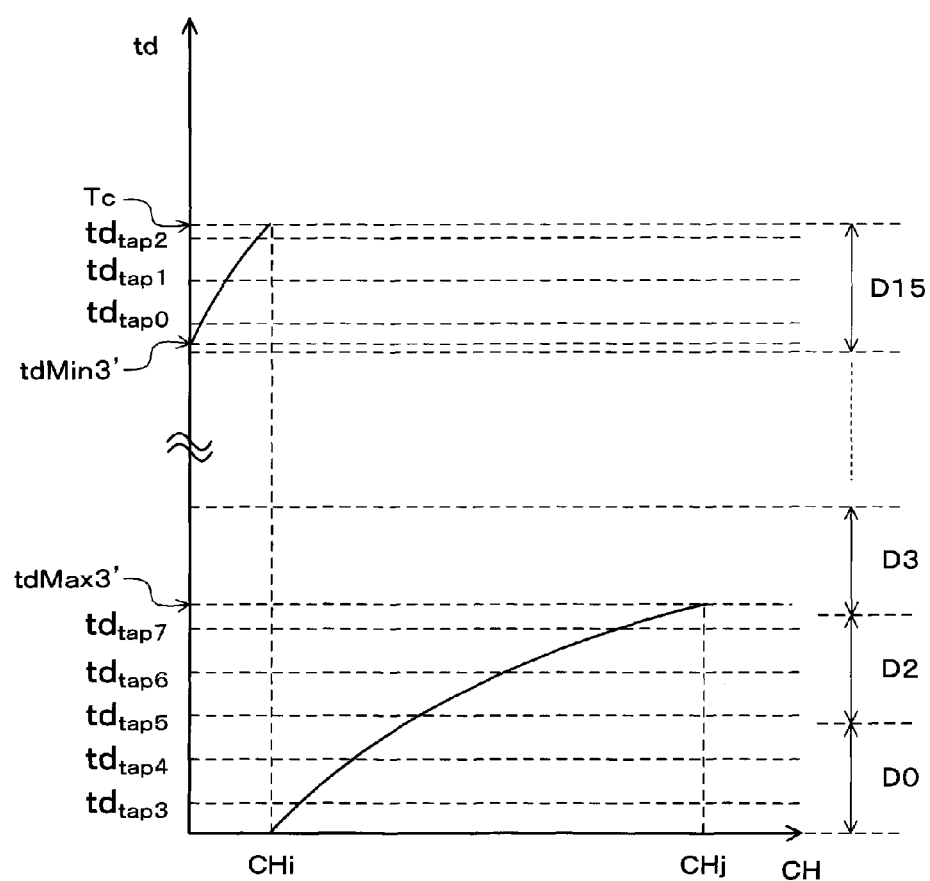
FIG. 10B is an example of a correspondence relationship between a representative delay amount and a quantized delay amount.
Figure 11A:
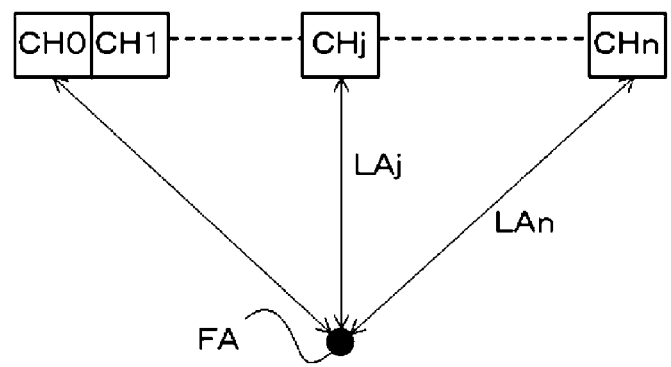
FIG. 11A is a diagram describing a positional relationship between the focus point and each transducer as well as a relationship with the delay amount to provide to each transducer.
Figure 11B:
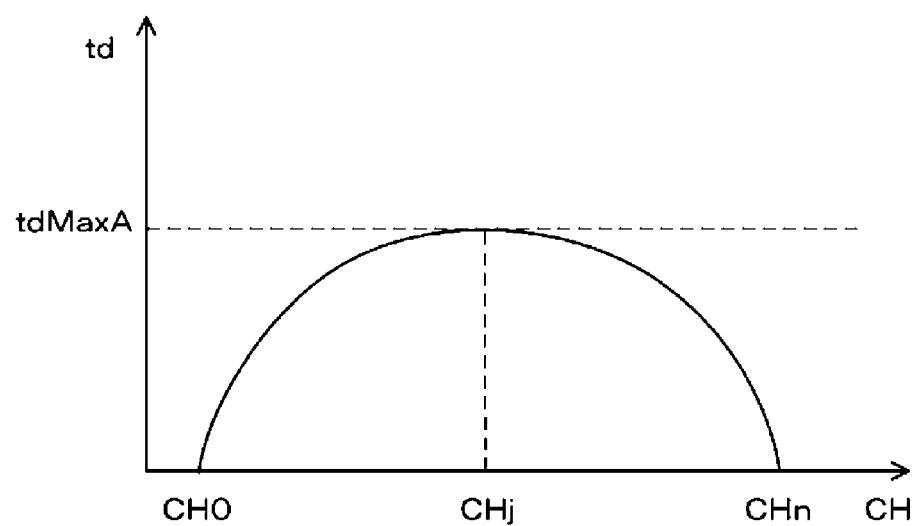
FIG. 11B is a diagram describing the positional relationship between the focus point and each transducer as well as the relationship with the delay amount to provide to each transducer.
Figure 12A:
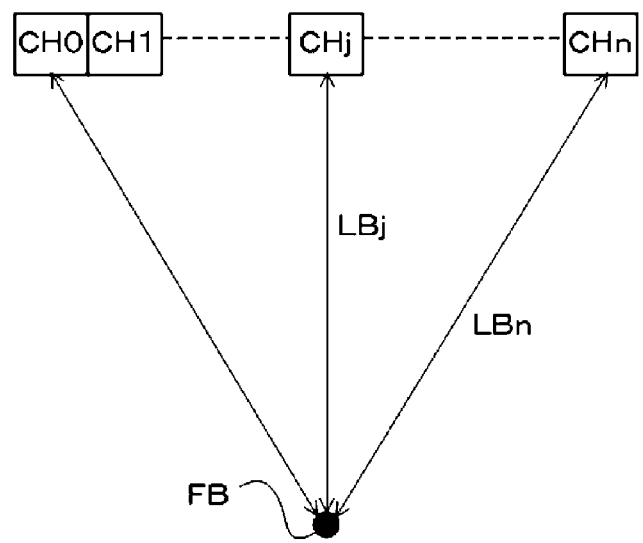
FIG. 12A is a diagram describing the positional relationship between the focus point and each transducer as well as the relationship with the delay amount to provide to each transducer.
Figure 12B:
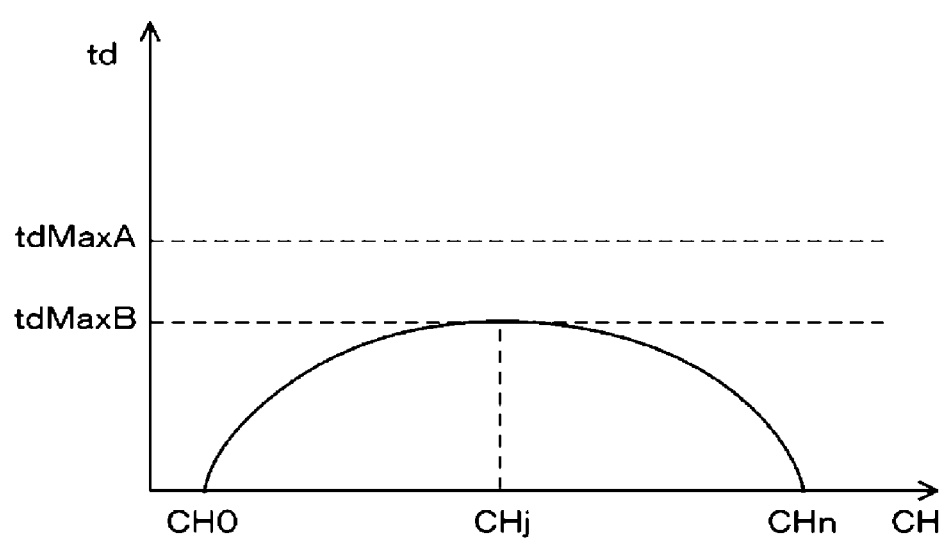
FIG. 12B is a diagram describing the positional relationship between the focus point and each transducer as well as the relationship with the delay amount to provide to each transducer.

In addition, by operating both the channel distributor 14 and the delay allocator 16 as described above, also for the case in which the time duration tD1yRange is present across two cycles $Tc_m$ and $Tc_{m+1}$, each tap and the quantized delay amount can be similarly related. For example, FIG. 10A and FIG. 10B are graphs showing the relationship between each transducer and the delay amount when the time duration tD1yRange is present across the two cycles $Tc_m$ and $Tc_{m+1}$. FIG. 10A shows an example of the correspondence relationship between the divided delay amount and each tap. Moreover, FIG. 10B shows an example of the correspondence relationship between the representative delay amount ($td_{tap0}$-$td_{tap7}$) and the quantized delay amount (D0-D15).

If the time duration tD1yRange is present across the two cycles $Tc_m$ and $Tc_{m+1}$, as shown in FIG. 10A, the delay amount corresponding to the channel CHi is defined to correspond to a transducer located between CH0 and CHn and is set to be equal to the cycle $Tc_m$, which is m times (m is an integer) as large as the cycle Tc of the ultrasound waves. In this case, the magnitude relationship between a maximum delay amount tdMax3, a minimum delay amount tdMin3, and the cycle $Tc_m$ will be tdMax3>$Tc_m$>tdMin3. In such a case, the magnitude relationship between tdMax3' and tdMin3', in which the maximum delay amount tdMax3 and the minimum delay amount tdMin3 have been each converted into the delay amount in one cycle of the ultrasound waves, and the cycle Tc, will be Tc>tdMin3'>tdMax3' as shown in FIG. 10B.

Also in such a case, the channel distributor 14 and the delay allocator 16 operate as described previously. That is, the channel distributor 14 calculates the time duration tD1yRange based on the delay amount corresponding to each transducer, i.e., the delay amount before quantization, divides the time duration tD1yRange, and then relates the resultant divided ranges to each tap. Subsequently, the delay allocator 16 specifies a representative value for the delay amount from the divided range, and calculates the representative delay amount $td_{tap0}$-$td_{tap7}$, which is the delay amount in one cycle of the ultrasound waves, based on this representative value. The delay allocator 16 compares the representative delay amount $td_{tap0}$-$td_{tap7}$ with each quantization range, and based on the comparison result thereof, relates each tap to the quantized delay amount. As described above, by operating both the channel distributor 14 and the delay allocator 16, the tap tap0-tap7 and the quantized delay amount D0-D15 are related as shown in FIG. 10B. That is, the output from tap0-tap2 is treated with delay processing based on the quantized delay amount D15. Moreover, the output from tap3 and tap4 is treated with delay processing based on the quantized delay amount D0, and the output from tap5-tap7 treated with delay processing based on the quantized delay amount D2.

As described above, with the ultrasound diagnosis apparatus according to the present embodiment and also in the case that there is a delay amount not used for delay processing of the received signals like the delay amount 0-tdMin2 in FIG. 8B, it is possible to thoroughly use the taps in the range of the delay amount (tdMin2-tdMax2) used for delay processing of received signals.

Although several embodiments of the present invention have been described, these embodiments are presented as examples and are not intended to limit the range of the invention. These novel embodiments can be implemented in other various forms, and various omissions, replacements, and changes are able to be made without departing from the scope of the invention. These embodiments and variations thereof are included in the range and scope of the invention, and also included in the range of the equivalents thereof described in Claims.

EXPLANATION OF SYMBOLS

1 Ultrasound diagnosis apparatus
10 Transmitter circuit
11 Group of ultrasound transducers
12 Amplifier circuit
13 Delay amount calculator
14 Channel distributor
15 Tap
16 Delay allocator
17 Adder circuit
18 Signal processor
19 Image processor
20 Display

The invention claimed is:

1. An ultrasound diagnosis apparatus comprising:
a plurality of ultrasound transducers configured to transmit continuous ultrasound waves toward a predefined focus point within a subject, and receive reflection waves reflected within the subject;
a plurality of taps configured to receive signals output from the plurality of ultrasound transducers;
a delay amount calculator circuit configured to calculate a first delay amount, being the time included in one cycle of the continuous ultrasound waves, for each of the ultrasound transducers based on the distance between the ultrasound transducer and the focus point;
a channel distributor circuit that is interposed between the ultrasound transducer and the tap, configured to select a minimum delay amount and a maximum delay amount from the first delay amount, divide the range from the minimum delay amount to the maximum delay amount by the number of the taps, relate each of the divided ranges to the tap, and input a signal output from the ultrasound transducer to the tap related to the divided range including the first delay amount corresponding to the ultrasound transducer; and a delay processor circuit configured to relate the time in which a maximum delay amount from a delay amount in one cycle of the continuous ultrasound waves is quantized by a predefined quantization number to the tap as a second delay amount, and performs delay processing on the signal input in each of the taps based on the second delay amount related to the tap.

2. The ultrasound diagnosis apparatus according to claim 1, wherein the channel distributor circuit is configured to add signals from two or more of the ultrasound transducers related to the first delay amount included in the divided range, and input the added signals to the tap related to the divided range.

3. The ultrasound diagnosis apparatus according to claim 2, wherein:
the plurality of ultrasound transducers are operated by separating the transducers into a transmitting region to transmit continuous ultrasound waves and a receiving region to receive ultrasound waves; and
the channel distributor circuit is configured to select the minimum delay amount and the maximum delay amount from the first delay amount corresponding to the ultrasound transducer included in the receiving region.

4. The ultrasound diagnosis apparatus according to claim 1, wherein:
the plurality of ultrasound transducers are operated by separating the transducers into a transmitting region to transmit continuous ultrasound waves and a receiving region to receive ultrasound waves; and
the channel distributor circuit is configured to select the minimum delay amount and the maximum delay amount from the first delay amount corresponding to the ultrasound transducer included in the receiving region.

5. The ultrasound diagnosis apparatus according to claim 1, wherein a larger number of the second delay amount is related to the taps by the delay processor circuit than the number of the taps.

6. The ultrasound diagnosis apparatus according to claim 3, wherein there a larger number of the second delay amount is related to the taps by the delay processor circuit than the number of the taps.

* * * * *